US00PP17938P2

(12) United States Plant Patent
Friday

(10) Patent No.: US PP17,938 P2
(45) Date of Patent: Aug. 21, 2007

(54) PEACH TREE NAMED 'P.F. LUCKY 12'

(50) Latin Name: *Prunus persica*
Varietal Denomination: P.F. Lucky 12

(76) Inventor: Paul Jan Friday, P.O. Box 850, Coloma, MI (US) 49038

( * ) Notice: Subject to any disclaimer, the term of this patent is extended or adjusted under 35 U.S.C. 154(b) by 0 days.

(21) Appl. No.: 11/401,491

(22) Filed: Apr. 11, 2006

(51) Int. Cl.
*A01H 5/00* (2006.01)

(52) U.S. Cl. ..... Plt./198

(58) Field of Classification Search ..... Plt./198
See application file for complete search history.

*Primary Examiner*—Kent Bell
*Assistant Examiner*—Annette H Para

(57) ABSTRACT

A new and distinct variety of peach, *Prunus persica,* tree having the following unique combination of desirable features.

1. Producing a very firm fruit having a resilient flesh texture.
2. Blossoms are non-showy when in full bloom.
3. A substantially spherical fruit with yellow flesh having a 3/16" wide then red flesh area that extends from the suture to the pit.
4. A mid-season peach ripens 3 days after 'Redhaven' (non-patented) which as large size and good storage and shelf life.

1 Drawing Sheet

Botanical classification: *Prunus persica.*

ORIGIN OF VARIETY

The new peach tree (hereinafter referred to as the 'P.F. Lucky 12") was originated by Paul Friday in an experimental orchard, which is maintained for the purposes of breeding peach trees, located in Coloma, Mich. Coloma is located in the southwest section of Michigan, USDA Hardiness Zone 6A, with observed temperature ranges of minus 12 degree Fahrenheit to 90 degree Fahrenheit, also with annual rainfall of about 40 inches.

In an ongoing mass-selection breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for their adaptability to local and regional growing conditions. Seeds resulting from open pollination of the trees in the experimental orchard are regularly planted in mass to produce new populations of seedlings, which are cultured and monitored to maturity. Trees with superior attributes are retained for further observation and testing and contribute seeds to advancing generations of new populations of seedlings.

The tree of this application, 'P.F. Lucky 12', was a selection from one such non-patented seedling population, and was based on the numerous superior genetic attributes of the tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in the experimental orchard, located in Coloma, Mich. The asexual propagation demonstrates that such reproduction of the characteristics of the tree are consistent and are established and transmitted through succeeding propagation.

SUMMARY OF THE VARIETY

The new and distinct variety of peach tree is of moderate upright growth and a regular and productive bearer of peaches. The blossoms are characterized by being contracted or partially spread when in full bloom.

The blossoms of the present peach tree at full bloom may be characterized as being non-showy. More specifically the blossom of the present peach tree have angularly spaced five blossom petal projecting upwardly at an inclined angle so as to form a blossom, having a diameter of about ¾" measured across the blossom. The typical non-showy blossom as exemplified for example by the 'Redhaven' (non-patented) peach tree, has five (5) radially extending and angularly spaced petals projecting upwardly at a relatively steep inclined angle so that the diametrical measurement across the outer edges of the petals is about ½".

The flesh of the fruit of the present peach tree is firm and is yellow with a thin red flesh area that extends from the suture to the pit.

The skin is smooth and is dark red color over almost 95 percent (95%) of its surface at full maturity. The fruit is large with an average diameter of 2¾".

It is noteworthy that the fruit of this tree is further characterized as having smooth, gently rounded cheeks at the blossom end of the fruit. These protrude to form fruit surfaces higher than the blossom point. This characteristic reduces fruit damage in harvest, shipping and storage, by reducing the exposure of and damage to the apical blossom protrusion in handling. This breaching of the skin and formation of an entry point for microorganisms which cause rot in many other commercially important peach varieties harvested in the same production period is avoided in this fruit.

The fruit has a firm flesh and may be described as resilient to the extent that the flesh is yieldable and restorable to its original state when subjected to impact forces, which may cause permanent deformities in peaches of the commercial varieties. The firmness of the fruit facilitates handling and packaging of the peach without damaging the same for shipment. This results in less spoilage and also increases the shelf life.

A peach which ripens 3 days after 'Redhaven' (non-patented) variety, which is high in red skin color and has exceptional firm flesh and large size fruit. When fully ripe a discerning characteristic develops which is a thin red flesh area 3/16" wide, that is present and extends from the suture to the pit.

BRIEF DESCRIPTION OF THE PHOTOGRAPHS

The accompanying photographic illustrations of a 6 year old tree of the new variety show the following:

The top photograph depicts leaves medium length, and width, having a notably very fine serrated margins. A tape measure is present, demonstrating the medium size of the leaves.

The bottom photograph depicts well-rounded fruit showing an unpronounced suture and a well-rounded blossom end. Two specimens of the fruit are bisected at a ninety-degree angle to the plane of the suture with the stone retained in half showing its freestone characteristic and yellow flesh and a thin red flesh area that is present from the suture to the pit. A tape measure is present indicating the large size of the fruit.

DESCRIPTION OF VARIETY

The detailed botanical description of the foliage and fruit of the new variety of peach tree is based upon observations of the specimens grown at Coloma, Mich. with the color terminology, other than the terminology expressed in common terms, are in accordance with the Pantone Matching System (PMS) as used internationally to identify printed colors.

Botanical classification: *Prunus persica* cultivar 'P.F. Lucky 12'.

Tree:
- *Age.*—Six (6) years.
- *Height.*—Unpruned 6'.
- *Width.*—Unpruned 8'.
- *Size.*—Medium.
- *Vigor.*—Medium.
- *Density.*—Medium.
- *Form.*—Spreading.
- *Production.*—Good.
- *Bearer.*—Excellent.
- *Disease resistance to bacterial leaf and fruit spot.*—Particularly resistant.

Trunk:
- *Bark.*—Pantone #499.
- *Size.*—Medium.
- *Diameter.*—2½" diameter at 15" above ground at 6 years of age.
- *Surface.*—Semi-rough.
- *Lenticels.*—Small — not noticeable.
- *Lenticels color.*—Pantone #156.
- *Lenticels size.*—⅛" to 5/16".

Branches:
- *Size.*—Medium 1½" diameter at 5" from trunk union.
- *Surface.*—Semi smooth.
- *Lenticels per square inch on branch.*—Nine (9).
- *Lenticels color.*—Pantone #155.
- *Lenticels size.*—1/16"-3/16".
- *Crotch angles.*—Natural 45 degree angles.
- *Branch color.*—Brown Pantone Color #160.
- *Internode length.*—1".

Leaves:
- *Size.*—7" long — 1½" wide.
- *Color.*—Adaxial (top) — Green Pantone #343.
- *Color.*—Abaxial (bottom) Green Pantone #364.
- *Form.*—Lanceolate.
- *Thickness.*—Medium.
- *Texture.*—Glabrous.
- *Margin.*—Finely serrated — not pronounced.
- *Petiole length.*—½".
- *Gland.*—1 on each side of petiole of leaf and at basal part of the leaf.
- *Gland color.*—Red.
- *Gland shape.*—Cupped.
- *Leaf base shape.*—Acute.
- *Leaf apex shape.*—Pointed.

Flower buds:
- *Size.*—5/16" long — ¼" wide.
- *Bud shape.*—Ovoid.
- *Color.*—Pink Pantone #243.

Flowers:
- *Blooming period.*—Apr. 19, 2005 to Apr. 25, 2005.
- *Bloom size.*—¾" diameter.
- *Bloom depth.*—⅝".
- *Size of petal.*—¾" long — 7/16" wide.
- *Number of petals.*—Five (5).
- *Petal color.*—Top of Petal — pink Pantone #250 — Bottom of Petal — pink Pantone #250.
- *Shape of petal.*—Ovate.
- *Petal margin.*—Smooth (Entire).
- *Petal base shape.*—Pointed.
- *Petal apex shape.*—Ovate.
- *Sepal size.*—¼" long — ⅛" wide.
- *Number of sepals.*—Five (5).
- *Sepal shape.*—Apex — pointed, base — ovate.
- *Sepal margin.*—Smooth (Entire).
- *Sepal color.*—Pantone #380.
- *Numbers of anthers.*—Twenty four (24).
- *Anthers color.*—Brown Pantone #138.
- *Number of stamens.*—Twenty four (24).
- *Stamen length.*—⅜".
- *Stamen color.*—Light yellow Pantone #100.
- *Pistil length.*—½".
- *Pistil color.*—Yellow Pantone #108.
- *Pollen.*—Present.
- *Flowers per cluster.*—Two (2).
- *Fragrance.*—None present.

Fruit:
- *Maturity when described.*—Firm Ripe.
- *Date of first picking.*—Aug. 3, 2005.
- *Date of last picking.*—Aug. 10, 2005.
- *Size.*—2¾" to 3" diameter.
- *Form.*—Spherical.
- *Suture.*—Not pronounced.
- *Weight.*—7.3 oz. to 8 oz.

Skin:
- *Thickness.*—Medium as compared to the species.
- *Texture.*—Medium as compared to the species.
- *Tendency to crack.*—None.
- *Down.*—Short as compared to the species.

*Color.*—Dark Red (Pantone #208) over 95%, with 5% or less yellow (Pantone #142) ground color.

Flesh:

*Texture.*—Firm, non-melting free of fiber.
*Ripens.*—Uniform.
*Flavor.*—Excellent.
*Aroma.*—Good.
*Eating quality.*—Very Good.
*Brix.*—13 brix.
*Color.*—Yellow — Pantone #155.
*Pit cavity color.*—Red — Pantone #208.

Stone:

*Type.*—Freestone.
*Size.*—1½" long, 1⅛" wide, ⅞" thick.
*Form.*—Ovoid.
*Base.*—Straight.
*Apex.*—Rounded but with a very sharp point.
*Sides.*—Uneven.
*Surface.*—Furrowed.
*Color.*—Brown Pantone #181.
*Tendency to crack.*—None.
*Kernel.*—9/16" long, ⅜" wide, ⅛" thick.
*Kernel taste.*—Bitter tasting.

Use: Dessert.
Shipping quality: Excellent.
Keeping quality: Very good.
Disease resistance: The fruit is resistant to brown rot.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree substantially as herein illustrated and described.

* * * * *

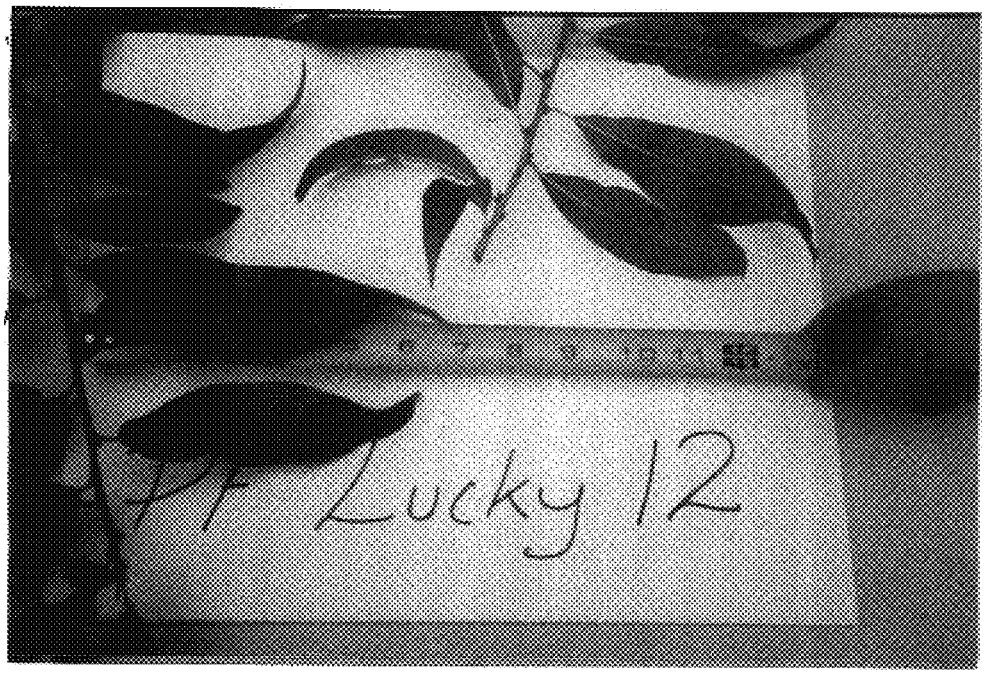
PF Lucky 12
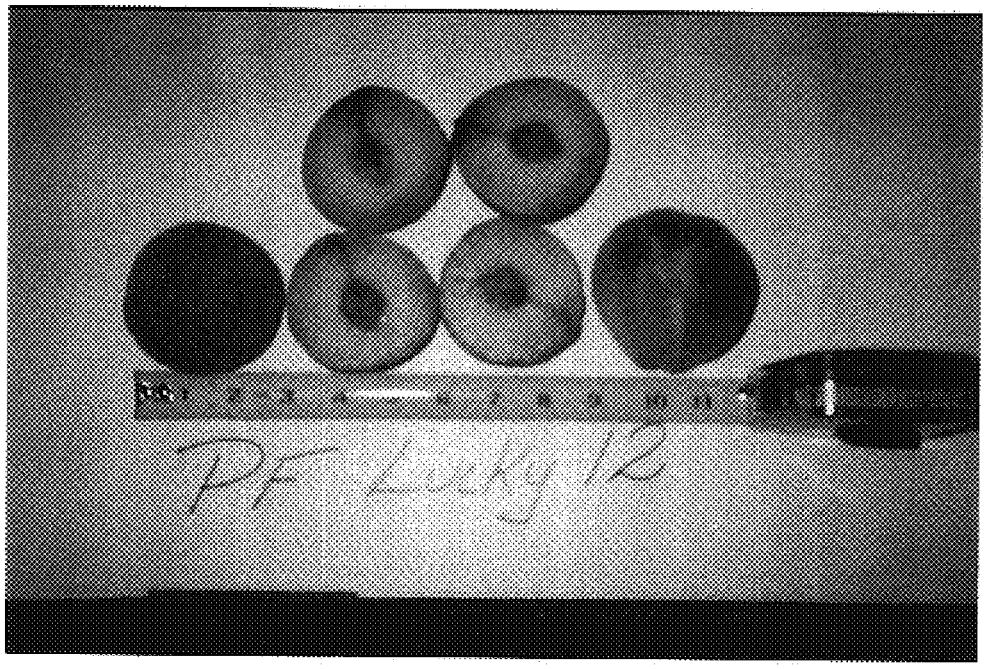
PF Lucky 12